(12) United States Patent
Kurian et al.

(10) Patent No.: US 12,079,583 B2
(45) Date of Patent: Sep. 3, 2024

(54) MACHINE LEARNING METHODS TO DETERMINE A LIKELIHOOD FOR AN EVENT TO OCCUR THROUGH SENTIMENT ANALYSIS OF DIGITAL CONVERSATIONS

(71) Applicant: Treasure Data, Inc., Mountain View, CA (US)

(72) Inventors: Thomas Kurian, Livermore, CA (US); Yasuyuki Kobayashi, Cupertino, CA (US); Asuka Ishii, Yokohama (JP); Korbboon Sathirakul, Tokyo (JP); Thanisorn Oon Pitipongsa, Tokyo (JP); Veer Vikram Singh Chauhan, Bangalore (IN)

(73) Assignee: Treasure Data, Inc., Mountain View, CA (US)

( * ) Notice: Subject to any disclaimer, the term of this patent is extended or adjusted under 35 U.S.C. 154(b) by 0 days.

(21) Appl. No.: 18/482,547

(22) Filed: Oct. 6, 2023

(65) Prior Publication Data
US 2024/0037341 A1   Feb. 1, 2024

Related U.S. Application Data

(63) Continuation of application No. 17/739,296, filed on May 9, 2022, now abandoned.

(30) Foreign Application Priority Data

Mar. 16, 2022 (IN) .............................. 202211014184

(51) Int. Cl.
*G16H 20/10* (2018.01)
*G06F 40/30* (2020.01)
(Continued)

(52) U.S. Cl.
CPC .......... *G06F 40/30* (2020.01); *G06Q 10/083* (2013.01); *G16H 20/10* (2018.01); *G06N 20/00* (2019.01)

(58) Field of Classification Search
CPC ................................................ G06Q 50/20–26
See application file for complete search history.

(56) References Cited

U.S. PATENT DOCUMENTS 11,056,242 B1 * 7/2021 Jain ........................ G16H 10/60
11,328,825 B1 * 5/2022 Yu .......................... G16H 50/20
(Continued)

OTHER PUBLICATIONS

Majumder Navonil et al., DialogueRNN: An attentive rnn for emotion detection in conversations, May 25, 2019, XP093062536, retrieved from the internet <https://arxiv.org/pdf/1811.00405.pdf> (retrieved Jul. 10, 2023), _ pages.
(Continued)

*Primary Examiner* — Neal Sereboff
(74) *Attorney, Agent, or Firm* — Baker Botts L.L.P.

(57) ABSTRACT

A computer-implemented method can comprise accessing a trained learning machine, evaluating, using the machine learning model, the transcript to output a first sentiment score related to the first party in the unique domain, accessing digital engagement data representing engagement of the first party with digital assets associated with the second party, evaluating the one or more sentiment score values and the digital engagement data to output a value indicative of a likelihood of the first party to take a particular action, and determining whether the value is above a threshold, and if so, automatically sending a notification to a computer device associated with the second party.

20 Claims, 4 Drawing Sheets

(51) Int. Cl.
 *G06Q 10/083* (2024.01)
 *G06N 20/00* (2019.01)

(56) References Cited

U.S. PATENT DOCUMENTS

| | | | |
|---|---|---|---|
| 2012/0191730 | A1 | 7/2012 | Parikh et al. |
| 2016/0283921 | A1* | 9/2016 | Ramanathan .......... G16H 10/60 |
| 2016/0316059 | A1* | 10/2016 | Nuta ..................... G06N 7/01 |
| 2016/0350651 | A1 | 12/2016 | Devarajan et al. |
| 2017/0278110 | A1* | 9/2017 | Ezry ................. G06Q 30/0201 |
| 2017/0323065 | A1 | 11/2017 | Proctor Beauchamp et al. |
| 2019/0180871 | A1* | 6/2019 | Doerflinger ............ G16H 50/20 |
| 2019/0392396 | A1* | 12/2019 | Liu .................... G06F 16/90332 |
| 2019/0392547 | A1* | 12/2019 | Katouzian .............. G06V 20/62 |
| 2020/0211716 | A1* | 7/2020 | Lefkofsky ............. G06F 18/214 |
| 2020/0380389 | A1 | 12/2020 | Eldeeb et al. |
| 2021/0049298 | A1* | 2/2021 | Suresh ................ G06F 18/2193 |
| 2021/0304857 | A1* | 9/2021 | Johansson ................ G06N 3/08 |
| 2021/0375272 | A1* | 12/2021 | Madwed ................ G06F 3/167 |

OTHER PUBLICATIONS

Wang Jiancheng et al., "Sentiment Classification in Customer Service Dialogue with Topic-Aware Multi-Task Learning," The Thirty-Fourth AAAI Conference on Artificial Intelligence (AAAI-20), Jan. 1, 2020, XP093062586, retrieved from the internet <https://ojs.aaai.org/index.php/AAAI/article/view/6454 (retrieved Jul. 10, 2023),—pages.
European Patent Office, EP Application No. 23162490.9-1203, Extended European Search Report dated Jul. 19, 2023, 12 pages.
B. Liu, Sentiment Analysis and Opinion Mining, Morgan & Claypool Publishers, May 2012, 168 pages.
Mark J. Van Der Laan, Entering the Era of Data Science: Targeted Learning and the Integration of Statistics and Computational Data Analysis, Advances in Stat. Analysis (2014), 20 pages.
Puja P. Pathak, Logistic Regression and Maximum Likelihood Estimation Function, Medium (Apr. 9, 2021), 9 pages.
Giuseppe Carleo et al., Machine Learning and the Physical Sciences, 91 Rev. of Modern Physics (2019), 47 pages.
Paul Ekman, "An Argument for Basic Emotions," Cognition and Emotion, 1992, 6 (3/4), 169-200, Lawrence Eribaum Associates Limited, 32 pages.
M.I. Jordan, et al, Machine learning: Trends, Perspectives, and Prospects, Science (2015), 7 pages.
Majumder Navonil et al., DialogueRNN: An attentive rnn for emotion detection in conversations, May 25, 2019, XP093062536, retrieved from the internet <https://arxiv.org/pdf/1811.00405.pdf> (retrieved Jul. 10, 2023), 8 pages.
Wang Jiancheng et al., "Sentiment Classification in Customer Service Dialogue with Topic-Aware Multi-Task Learning," The Thirty-Fourth AAAI Conference on Artificial Intelligence (AAAI-20), Jan. 1, 2020, XP093062586, retrieved from the internet <https://ojs.aaai.org/index.php/AAAI/article/view/6454 (retrieved Jul. 10, 2023), 8 pages.

* cited by examiner

MACHINE LEARNING METHODS TO DETERMINE A LIKELIHOOD FOR AN EVENT TO OCCUR THROUGH SENTIMENT ANALYSIS OF DIGITAL CONVERSATIONS

BENEFIT CLAIM

This application claims the benefit under 35 U.S.C. § 120 as a Continuation of application Ser. No. 17/739,296, filed May 9, 2022, which claims the benefit under 35 U.S.C. § 119 of Indian patent application 202211014184, filed Mar. 16, 2022, the entire contents of which are hereby incorporated by reference for all purposes as if fully set forth herein.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright or rights whatsoever. © 2021-2022 Treasure Data, Inc.

TECHNICAL FIELD

One technical field of the present disclosure is natural language processing including machine analysis of transcripts of conversations. Another technical field is machine learning including classifiers to predict the likelihood of an event to occur through sentiment analysis of digital conversations.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

Enterprises have large-scale databases related to client data and to potential client data. In some fields, an enterprise may have complex data that relates to the geography of clients and potential clients, rules and regulations associated with each of the clients and potential clients, the propensity of the clients or potential clients to use particular products of the enterprise, and records of interactions between representatives of the enterprise and the clients or potential clients. Examples of interactions can include transcripts of conversations and records of email correspondence. All of this data may be stored in an organized table with the database or within objects created by a server of the enterprise. However, the magnitude of the data does not allow for the enterprise to efficiently determine the supply chain of the products in order to maximize efficiency of the enterprise operations.

Therefore, an automated method of inspecting this data along with updating the data to determine whether an event is likely to occur is needed. For example, agents of the enterprise may have multiple meetings with multiple clients or potential clients in a single day. The records of these interactions would be impossible for enterprise to sort through to predictively react. As such, an automated method of analyzing these records to predict events and react accordingly is needed to improve the operation of the enterprise and its supply chain.

A particular challenge arises in the pharmaceutical industry, in which meetings between the pharmaceutical company's commercial teams and healthcare professionals have changed to substantially digital online meetings on video platforms like ZOOM or MICROSOFT TEAMS. For example, a secular trend in the pharmaceutical industry has been the decline of physical, in-person meeting times and a decrease in the frequency of meetings of commercial teams and health care providers (HCP) over the past decade. Moreover, such meetings also have become shorter under stress conditions such as pandemic conditions; during the COVID-19 pandemic, the median time of such meetings declined to eight to fourteen minutes. At the same time the impact on prescribing a pharmaceutical composition, after the digital meeting, has become unpredictable, and often has declined or become less effective compared to physical in-person meetings. Consequently, there is an acute need in the pharmaceutical field to find ways to analyze the artifacts of digital meetings, such as transcripts, and predict prescribing behavior or determine what changes in the digital meetings are needed based on an analysis of the sentiment of the artifacts of the digital meetings to result in changes in prescribing behavior.

SUMMARY

The appended claims may serve as a summary of the invention.

DETAILED DESCRIPTION

Figure 1:
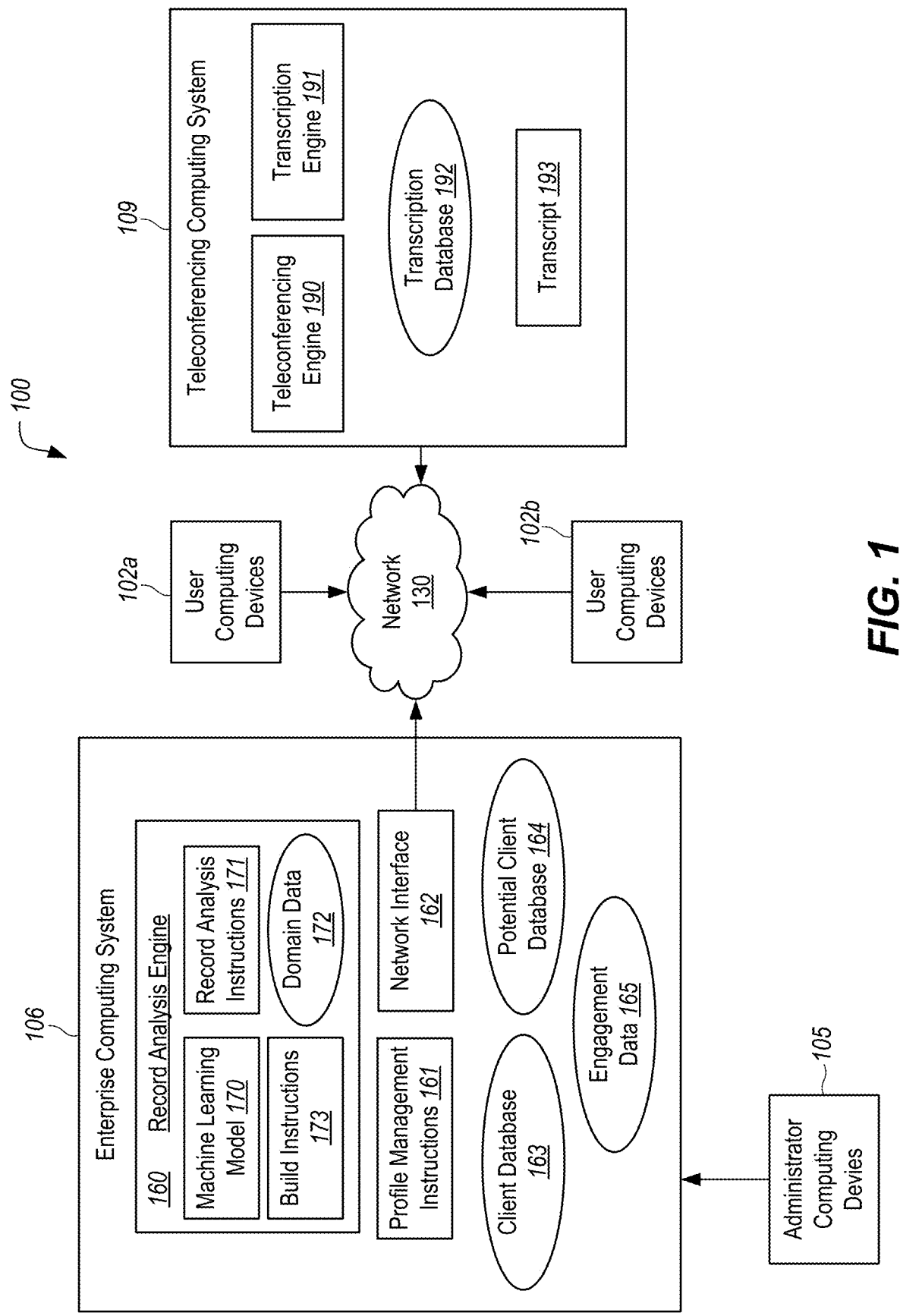
FIG. 1 illustrates a distributed computer system showing the context of use and principal functional elements with which one embodiment could be implemented.

In the following description, for the purposes of explanation, numerous specific details are set forth to provide a thorough understanding of the present invention. It will be apparent, however, that the present invention may be practiced without these specific details. In other instances, well-known structures and devices are shown in block diagram form to avoid unnecessarily obscuring the present invention.

The text of this disclosure, in combination with the drawing figures, is intended to state in prose the algorithms that are necessary to program a computer to implement the claimed inventions, at the same level of detail that is used by people of skill in the arts to which this disclosure pertains to communicate with one another concerning functions to be programmed, inputs, transformations, outputs and other aspects of programming. That is, the level of detail set forth in this disclosure is the same level of detail that persons of skill in the art normally use to communicate with one another to express algorithms to be programmed or the structure and function of programs to implement the inventions claimed herein.

Embodiments are described in sections below according to the following outline:
1. General Overview
2. Structural & Functional Overview
   2.1 Example Distributed System Architecture
   2.2 Example Method of Determining Likelihood of an Event Based on Record Data
   2.3 Benefits and Improvements
3. Implementation Example—Hardware Overview 1. General Overview Embodiments can enable data scientists, data engineers, and members of machine language teams to transform raw transcript data into sentiment scores and further use the sentiment score(s) with other engagement data in order to predict the likelihood of an action or event and to act. One specific application is deriving the propensity of a healthcare professional to prescribe a pharmaceutical composition after conducting a digital meeting with representatives of a pharmaceutical company that makes and/or sells the composition. Embodiments can be programmed to derive a sentiment score for a healthcare professional (HCP) based on machine analysis of meeting transcription data of a digital meeting by analyzing the text and deriving sentiment or emotion. In some embodiments, emotion or sentiment is classified according to six innate human emotions as defined in the Ekman Taxonomy of Universal Emotions, which comprise sadness, anger, contempt, disgust, surprise, and fear, as well as additional states like agreement. In some embodiments, the sentiment score may be representative of the overall state of the meeting sentiment on a negative (e.g., unhappy or unlikely to take an action) to a positive (e.g., happy or likely to take the action) spectrum (e.g., on a scale from −1 to 1, respectively). The sentiment score can be joined with additional digital engagement data relating to digital advertisements, websites, or other computer-based communications of the HCP, to predict via machine learning models the propensity of an HCP to prescribe a pharmaceutical composition after each digital meeting, and/or whether the propensity is increasing or decreasing. In some embodiments, the additional engagement data may include data or digital artifacts (e.g., transcripts) from previous meetings that are analyzed relative to and/or compared to the sentiment score in order to provide an understanding of the overall sentiment of the respective party. In some embodiments, output of the machine learning models can classify, predict, or output the next best recommendations to the commercial teams to act, for example, setting up an in-person meeting.

In one embodiment, a computer-implemented method, comprises accessing a trained machine learning model, the machine learning model having been trained on domain data unique to a unique domain, the machine learning model having been trained to accept transcript data as an input, predict or classify emotional content of one or more portions of the transcript related to a first party, and output a sentiment score, the sentiment score representing a likelihood of the first party to take an action, establishing a programmatic connection between a first computer and a second computer, receiving, at the second computer from the first computer using the programmatic connection, a natural language transcript of a conversation between the first party and a second party, evaluating, using the machine learning model, the transcript to output a first sentiment score related to the first party in the unique domain, accessing digital engagement data representing engagement of the first party with digital assets associated with the second party, evaluating the one or more sentiment score values and the digital engagement data to output a value indicative of a likelihood of the first party to take a particular action, and determining whether the value is above a threshold, and if so, automatically sending a notification to a computer device associated with the second party.

In some embodiments, the method also includes automatically submitting an order to the second computer if the value is above the threshold, the order specifying shipping a product associated with the action or event to the first party. The method also includes receiving, at the second computer from the first computer, a second natural language transcript of a second conversation between a first party and a second party.

In an embodiment, the method also includes evaluating, using the machine learning model, the second natural language transcript to output a second sentiment score related to the first party in the domain associated with the second party, automatically updating the value with the second sentiment score, determining whether the value is above the threshold, and if so, automatically sending a notification to a computer device associated with the second party. Alternatively or additionally, the method may include building the trained machine learning model by selecting the domain data from a database, selecting a machine learning type based on information regarding the first party and the second party, and training the selected machine learning type with the domain data to build the machine learning model.

In some embodiments, the domain data being selected based at least on a field associated with the second party, a geographic location of the first party, and a geographic location of the second party. Alternatively or additionally, the domain data may include words and phrases that each have associated flags, the flags indicating emotional data or classifications of the words and phrases. In various embodiments, the emotional data or classifications including information related to categories that include sadness, anger, contempt, disgust, surprise, fear, and agreeableness.

Moreover, the method may include filtering the natural language transcript to exclude data related to portions of the natural language transcript that indicative of the second party talking. Alternatively or additionally, the first party may be a healthcare provider, the action comprising the first party writing a prescription for a particular pharmaceutical composition.

In another embodiments, one or more non-transitory computer-readable storage media storing one or more sequences of program instructions which, when executed using one or more processors, cause the one or more processors to execute, accessing a trained machine learning model, the machine learning model having been trained on domain data unique to a unique domain, the machine learning model having been trained to accept transcript data as an input, predict or classify emotional content of one or more portions of the transcript related to a first party, and output a sentiment score, the sentiment score representing a likelihood of the first party to take an action, establishing a programmatic connection between a first computer and a second computer, receiving, at the second computer from the first computer using the programmatic connection, a natural language transcript of a conversation between the first party and a second party, evaluating, using the machine learning model, the transcript to output a first sentiment score related to the first party in the unique domain, accessing digital engagement data representing engagement of the first party with digital assets associated with the second party, evaluating the one or more sentiment score values and the digital engagement data to output a value indicative of a likelihood of the first party to take a particular action, and determining whether the value is above a threshold, and if so, automatically sending a notification to a computer device associated with the second party.

In some embodiments, the storage media may also include sequences of program instructions which, when executed using the one or more processors, cause the one or more processors to execute, automatically submitting an order to the second computer if the value is above the threshold, the order configured to ship a product associated with the action or the event to the first party.

In some embodiments, the storage media may also include sequences of program instructions which, when executed using the one or more processors, cause the one or more processors to execute, receiving, at the second computer from the first computer, a second natural language transcript of a second conversation between a first party and a second party, or evaluating, using the machine learning model, the second natural language transcript to output a second sentiment score related to the first party in the domain associated with the second party, automatically updating the value with the second sentiment score, and determining whether the value is above the threshold, and if so, automatically sending a notification to a computer device associated with the second party.

In some embodiments, the storage media may also include sequences of program instructions which, when executed using the one or more processors, cause the one or more processors to execute, building the machine learning model comprises selecting the domain data from a database, selecting a machine learning type based on information regarding the first party and the second party, and training the selected machine learning type with the domain data to build the machine learning model. In an embodiment, the domain data selected based at least on a field associated with the second party, a geographic location of the first party, and a geographic location of the second party. Alternatively or additionally, the machine learning model may be unique to a domain specific to the first party and the second party and the emotional data or classifications may include information related to categories that include sadness, anger, contempt, disgust, surprise, fear, and agreeableness. In various embodiments, the action comprises the first party purchasing or prescribing a particular product of the second party.

In another embodiment, a server system of an enterprise may include, a network interface, one or more processors coupled to the network interface, one or more memory devices coupled to the one or more processors, wherein the one or more memory devices comprises a database configured to store information regarding clients of the enterprise, information regarding potential clients of the enterprise, and information regarding a domain of the enterprise. The one or more memory devices are further configured to store one or more sequences of program instructions which, when executed using one or more processors, cause the one or more processors to execute accessing a trained machine learning model, the machine learning model having been trained on domain data unique to a unique domain, the machine learning model having been trained to accept transcript data as an input, predict or classify emotional content of one or more portions of the transcript related to a first party, and output a sentiment score, the sentiment score representing a likelihood of the first party to take an action establishing a programmatic connection between a first computer and a second computer, receiving, at the second computer from the first computer using the programmatic connection, a natural language transcript of a conversation between the first party and a second party, evaluating, using the machine learning model, the transcript to output a first sentiment score related to the first party in the unique domain, accessing digital engagement data representing engagement of the first party with digital assets associated with the second party, evaluating the one or more sentiment score values and the digital engagement data to output a value indicative of a likelihood of the first party to take a particular action, and determining whether the value is above a threshold, and if so, automatically sending a notification to a computer device associated with the second party.

The foregoing embodiments, features, and aspects are examples of the subject matter of the disclosure and other embodiments, features, and aspects will be apparent from other sections of the disclosure.

2. Structural & Functional Overview 2.1 Example Distributed System Architecture

FIG. 1 illustrates a distributed computer system showing the context of use and principal functional elements with which one embodiment could be implemented.

In an embodiment, a computer system 100 comprises components that are implemented at least partially by hardware at one or more computing devices, such as one or more hardware processors executing stored program instructions stored in one or more memories for performing the functions that are described herein. In other words, all functions described herein are intended to indicate operations that are performed using programming in a special-purpose computer or general-purpose computer, in various embodiments. FIG. 1 illustrates only one of many possible arrangements of components configured to execute the programming described herein. Other arrangements may include fewer or different components, and the division of work between the components may vary depending on the arrangement.

FIG. 1, and the other drawing figures and all of the description and claims in this disclosure, are intended to present, disclose and claim a technical system and technical methods in which specially programmed computers, using a special-purpose distributed computer system design, execute functions that have not been available before to provide a practical application of computing technology to the problem of machine learning model development, validation, and deployment. In this manner, the disclosure presents a technical solution to a technical problem, and any interpretation of the disclosure or claims to cover any judicial exception to patent eligibility, such as an abstract idea, mental process, method of organizing human activity or mathematical algorithm, has no support in this disclosure and is erroneous.

In an embodiment, a plurality of user computers 102a, 102b, administrator computers 105, teleconferencing computing system 109, and network 130 are communicatively coupled to an enterprise computing system 106. Each of the user computers 102a, 102b and administrator computers 105 comprises any of a desktop computer, laptop computer, tablet computer, smartphone, or other computing device and may be coupled directly or indirectly via one or more network links. User computers 102a, 102b can be associated with end users who interact with programs of provided by the teleconferencing computing system 109 and/or the enterprise computing system 106 to generate natural language transcript data and other engagement data as described herein. Administrator computers 105 can be associated with other end users who are responsible to configure, manage, or administer the enterprise computing system 106.

In an embodiment, the network 130 can be one or more local area networks, wide area networks, or internetworks, using any of wired or wireless, terrestrial or satellite data links. In an embodiment, the enterprise computing system 106 and the teleconferencing computing system 109 comprise networked computers that can be called or instructed to cause dispatching communications to user computers 102*a*, 102*b* or other entities in the manner described in other sections herein.

The enterprise computing system 106 includes a record analysis engine 160, profile management instructions 161, a network interface 162, a client database 163, a potential client database 164, and/or an engagement data database 165. A commercially available example of enterprise computing system 106 is the TREASURE DATA customer data platform (CDP) from Treasure Data, Inc. and Treasure Data K.K. The network interface 162 is a device structured to allow the enterprise computing system 106 and associated components to communicate with the other devices via the network. For example, network interface 162 is coupled to the engines, instructions, and databases described with reference to the enterprise computing system 106 and communicatively couples the enterprise computing system to the network 130. Functionally, network interface 162 provides a means of integrating enterprise computing system 106 with other systems such as the teleconferencing computing system 109.

The record analysis engine 160 comprises a sequence of executable stored instructions that are organized in functional units, packages, and elements that are executed to accomplish the operations and steps described herein. In an embodiment, the record analysis engine 160 comprises a machine learning model 170, record analysis instructions 171, build instructions 173, and/or domain data 172.

The machine learning model 170 is a trained machine learning model that has been built, for example, using the build instructions 173 and is accessible by the enterprise computing system 106 to generate sentiment data related to natural language text. For example, the machine learning model 170 may be FLARE, which is described at the time of this writing in the sub domain "flare" of the domain "readthedocs.io" on the World Wide Web, or the spaCy natural language processing library that integrates with the PYTHON environment. FLARE is well suited to use with Japanese language transcripts. Or, the machine learning model can be any of transformer-based machine learning models such as BERT, RoBERTa models, or ClinicalBERT models. Moreover, the machine learning model 170 may be unique to the enterprise, unique the enterprise and a particular client, entity, or other party, or unique to a particular product of the enterprise and/or a particular party.

In some embodiments, the machine learning model 170 is unique because the model has been trained with domain data 172 specific to the product, enterprise, and/or particular party. For example, different fields of healthcare or pharmaceuticals may use specialized scientific, medical, or technical terminology that is represented in training datasets to train the machine learning model 170. Experiments have shown that generic data, such as from WIKIPEDIA or other generic public sources, is less effective than domain-specific training data, specifically data representing conversations in the relevant domain. Training datasets can comprise labeled conversations in the same or different domains and can use data from a CDP that has been obtained other than from transcripts. Further, with a sufficient training dataset, one machine learning model 170 can accurately output predictions that take into account all the six innate human emotions as defined in the Ekman Taxonomy of Universal Emotions, as well as additional states like agreement. Embodiments are not required to use the Ekman Taxonomy and can simply classify a change in sentiment, as compared to the sentiment of a prior meeting, as trending from negative to positive using a real number scale of −1 to +1. In some embodiments, the machine learning model 170 may include one or more machine learning models. For example, the machine learning model 170 may include the trained machine learning model and a machine learning classifier.

The record analysis instructions 171 are instructions that, when executed, allow the record analysis engine 160 to analyze a natural language transcript to generate transcript data that can be evaluated by the machine learning model 170. For example, the record analysis instructions 171 may identify each person and/or associated party in the transcript. In some embodiments, the record analysis instructions 171 may filter out portions of the transcript, for example, by excluding portions of the transcript that are associated with agents of the enterprise or other selected party. In some embodiments, the record analysis instructions 171 may determine or select from memory the particular machine learning model 170 to use in order to accurately evaluate the transcript data. For example, the record analysis instructions 171 may identify the users that appear in the transcript, identify the parties, organizations, or enterprises associated with each of the users that appear in the transcript, and select a trained machine learning model 170 from a list of previously built and stored machine learning models that is unique to the parties, organizations, enterprises, or particular user. In some embodiments, for example, where the record analysis instructions 171 cannot identify a suitable trained machine learning model 170 for a particular transcript, the record analysis instructions 171 may request a model to be built from an external computing device or cause the build instructions 173 to execute in order to build a suitable machine learning model 170.

The build instructions 173 comprise instructions that, when executed by one or more processors, cause the enterprise computing system 106 to build a particular machine learning model 170. The build instructions 173 comprise instructions to identify and select a particular type of machine learning model, identify and select domain data 172 for the particular machine learning model, which may be based on the transcript data and/or the parties or organizations within the transcript, and train the selected machine learning model using the selected domain data 172. For example, the build instructions 173 may identify and select a type of machine learning model from among those specified herein based on the transcript data, a first party associated with the transcript, a second party associated with the transcript data, and/or both the first and second party. In some embodiments, the build instructions 173 selects the type of machine learning model from a list of machine learning models by referencing a look-up table that indicates the best type of machine learning model for the first and/or second party. The build instructions 173 may identify the domain data 172 based on the transcript, a language of the transcript, an identification of the first party, a geographic location of the first party, an identification of the second party, a geographic location of the second party, and/or an identification of a particular user or person that appears in the transcript. For example, the build instructions 173 may follow one or more predefined rules to identify information in the transcript and use a lookup table to select data elements from the domain data 172 that will be used to train or build the machine learning model 170 unique to the information identified. Example information that can be identified includes language, parties, locations of the parties. In some embodiments, the build instructions 173 fine-tunes or trains the model to build the trained model. For example, the build instructions 173 may fine tune the model by selecting the domain data 172 particular to the application in which the model is being deployed. In some embodiments, the application may be a health care pharmaceutical setting in which is unique features (e.g., words, phrases, etc.) from the understanding of conversations between pharma commercial brands and health care providers comprise the selected domain data and are used to fine tune or train the machine learning model, which results in a unique model focused on accuracy and efficiency with regard to the application that the model is being deployed. In some embodiments, the machine learning model may be built and stored as a trained machine learning model 170 for various different modalities. For example, the machine learning models may be trained or fine-tuned with application-specific training to different digital conversation modalities such as chatbots, real-time speech recognition, transcript data, etc.

The domain data 172 is a repository that includes a plurality of variable and associated flags. In some embodiments, the domain data 172 may be structured as a data table. The plurality of variables may each include a word or phrase and one or more associated scores. The one or more associated scores may be unique to a category of emotional or classification data. For example, the domain data 172 may include a first variable stored as a string that includes the phrase "I like that" may be associated with a happiness score, a sadness score, an agreeable score, or any other category of emotional data that is determined to be relevant. In some embodiments, each variable of the domain data 172 may be associated or indicated as belonging to a particular language, a particular party, a particular geographic location, and so on that may be used by the build instructions to select the relevant domain data 172 for a particular build. In some embodiments, the domain data 172 is created or uploaded by an administrator. In some embodiments, the domain data 172 may be created or updated using a recursive learning machine model.

The client database 163 and the potential client database 164 are data repositories that contain information regarding a list of clients and potential clients, respectively. For example, the database may store information in a tabular structure or an object structure that associates a client or potential client with information related thereto. For example, in some embodiments the information may include a geographic location, a list of personnel or agents, a language, a list of physical locations, history with the enterprise including prior purchases, and/or prior samples sent to each of the clients and potential clients.

The engagement data database 165 is a data repository that includes information regarding the history of interactions of a particular party with digital assets of the enterprise. The particular party can be a client or potential client. For example, the engagement data may include written records, such as emails from or to the respective party, calendar records that specify users, accounts, or parties in meetings, information regarding interactions between a computing system of the particular party and the enterprise computing system, information regarding the amount of time a user from the particular party has spent on a website associated with the enterprise, a number of times that the particular party has requested information, and the type of information provided, and so on. The engagement data allows for the enterprise to update information for each client or potential client based on the engagement of one or more users associated with the client or potential client with digital assets such as websites, webinars, and email lists. In some embodiments, the engagement data database 165 may include engagement data that is flagged for various digital conversation modalities. For example, some objects in the database may be unique to short-hand terms or slang unique to a particular context and, for example, a chat box modality.

The profile management instructions 161 comprise instructions that, when executed by one or more processors, cause the enterprise computing system 106 to manage the profile associated with the enterprise, the clients, and/or the potential clients. For example, the profile management instructions 161 may receive or identify engagement data based on an interaction with the digital assets of the enterprise, associate the engagement data with a particular client or potential client, and update the engagement data database 165, the client databases 163, or potential client databases 164 based thereon. In some embodiments, the profile management instructions 161 may receive records such as emails, associate the record with a particular party, and automatically update the engagement data database 165 to include the record.

The teleconferencing computing system 109 includes a teleconferencing engine 190 that comprises machine readable instructions that, when executed by one or more processors of the teleconferencing computing system 109, allow the teleconferencing computing system 109 to communicably couple a first user computing device of the user computers 102a with a second user computing device of the user computers 102b. For example, the teleconferencing engine 190 may connect the first user computing device to the second computing device via the network 130. In some embodiments, the first user computer 102a may display a web application, a mobile application, or other type of computer application page that allows a first user on the first user computing device to virtually conference with a second user on the second user computing device. In some embodiments, the teleconferencing engine 190 is configured to allow multiple computing devices and users to join a virtual chatroom. Examples of teleconferencing computing system 109 include the computers that support the commercial services ZOOM, MICROSOFT TEAMS, BLUEJEANS, GOOGLE MEET, and functionally similar systems.

In some embodiments, the teleconferencing computing system 109 includes a transcription engine 191 that transcribes conversations between users in a virtual conference in a natural language transcript. For example, the transcription engine 191 may identify portions of the conference that are associated with each user by monitoring noise data coming from each of the user computers 102a, 102b, associating the noise data with the respective user computers 102a, 102b and there by a user based on credentials used to access the teleconference), and performing a machine learning algorithm on the noise in order to transform the noise into natural language text. The transcription engine 191 may create a record of the virtual teleconference by storing the natural language transcript for a particular virtual conference, or a portion thereof, within the transcription database 192. In some embodiments, a transcript 193 is created for each virtual conference and stored in the transcription database 192. The transcript 193 may be created in real time as the noise data from the virtual conference is received by the teleconferencing computing system 109 or created in a post processing step by feeding audio recording data of the virtual conference into the transcription engine 191.

The foregoing is a generalized and broad description of the operations of the enterprise computing system 106, in one embodiment. A complete description of all possible operations and uses of the enterprise computing system 106 is beyond the scope of this disclosure and would obscure the focus of this disclosure.

2.2 Example Method of Determining Likelihood of an Event Based on Record Data

Figure 2:
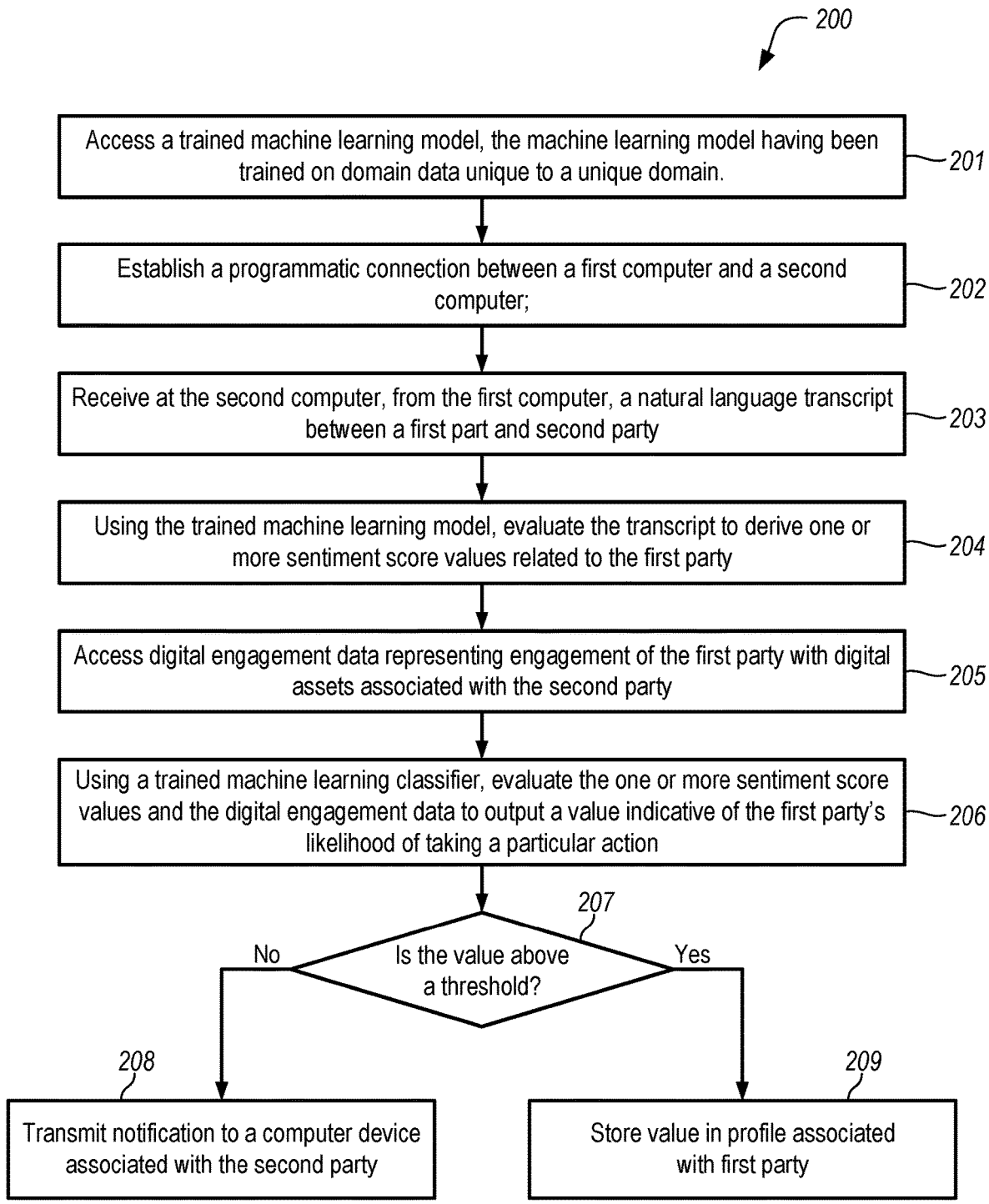
FIG. 2 illustrates the system of FIG. 1 with a focus on exploratory data analysis instructions and database tables of one implementation.

FIG. 2 illustrates an example computer-implemented process or algorithm for determining the likelihood of an event based on record data. FIG. 2 and each other flow diagram herein is intended as an illustration at the functional level at which skilled persons, in the art to which this disclosure pertains, communicate with one another to describe and implement algorithms using programming. In an embodiment, the event is a first party or agent of the first party taking a particular action. In some embodiments, the particular action may be associated with a product of the enterprise or propensity of the first party to use or prescribe the product. In some embodiments, the product is a pharmaceutical product.

The flow diagrams are not intended to illustrate every instruction, method object or sub-step that would be needed to program every aspect of a working program, but are provided at the same functional level of illustration that is normally used at the high level of skill in this art to communicate the basis of developing working programs.

In the example of FIG. 2, a computer-implemented process 200 initiates execution at block 201 where a trained machine learning model is accessed. It is to be appreciated that while FIG. 2 is discussed with reference to a transcript and transcript data, that in alternative embodiments, different artifacts or modalities of digital conversations may also be implemented. For example, a second computer such as the enterprise computing system 106 may be programmed to select a trained machine learning model that is unique to a domain with which a particular transcript is a part of. In some embodiments, the selected trained machine learning model is unique to a domain associated with an enterprise and/or clients or potential clients thereof. The trained machine learning model has been trained to accept transcript data that includes information regarding a first party and a second party as an input, predict or classify emotional content of one or more portions of the transcript related to a party, and output a sentiment score, the sentiment score representing a likelihood of the first party to take a particular action. In some embodiments, the trained machine learning model is selected from a database comprising multiple trained machine learning models. In some embodiments, the trained machine learning model is selected based on an identity of the first party and the second party, or agents thereof. In some embodiments, the trained machine learning model may be built, for example, as described with reference to FIG. 3.

At block 202 a programmatic connection between a first computer and a second computer is established. For example, block 202 can be programmed to establish a connection between the teleconferencing computing system 109 and the enterprise computing system 106. In some embodiments, the programmatic connection is made via a network using, for example, an application protocol interface (API), an app-specific protocol, or a parametrized HTTP call. The particular means of programmatic connection is not critical provided that enterprise computing system 106 has a means of electronically requesting and receiving data from the teleconferencing computing system 109.

At block 203 the second computer retrieves or receives a natural language transcript between a first party and a second party. For example, the second computer retrieves or receives a natural language transcript between one or more agents of the enterprise and one or more agents of another enterprise. The transcript could be, for example, a digitally stored electronic transcript of an audiovisual call or teleconference call between one or more representatives of an HCP and one or more representatives of a manufacturer or seller of a pharmaceutical composition. The transcript can be natively and automatically created, using speech-to-text techniques, and stored in electronic digital format, by the teleconferencing computing system 109. In some embodiments, the second computer requests the natural language transcript via a particular programmatic call function that includes an identification of the requested transcript, an identification of the first party, and/or an identification name of the second party. In some embodiments, the second computer can retrieve the transcript directly from a database of the first computer. In some embodiments, the natural language context includes additional metadata such as usernames or identifications of users that appear in the transcript, timestamps, duration of the virtual conference, etc.

At block 204, the trained machine learning model is used to evaluate the transcript to output a first sentiment score related to the first party in the domain associated with the second party. For example, the second computer may transform the transcript into discrete structured data elements and/or filter data from the transcript. In one example, the second computer may filter out all transcript data that is associated with the second party or a particular user. In another example, the second computer may parse through the transcript data and break down the information into structured data elements that are each associated with either the first party or the second party and include the data that was parsed and identified.

The transcript data is evaluated using the trained machine learning model that outputs the first sentiment score based on predicted or classified emotional content associated with the transcript data. For example, predicted or classified emotional content may include scores for emotional categories such as anger, sadness, agreeableness, contempt, disgust, surprise, fear, etc. The trained machine learning model may evaluate all the transcript data, for example, using single shot detection (SSD) and automatically output the first sentiment score representing a likelihood of the first party to perform a particular action. For example, in some embodiments, the particular action may be the purchase of a particular product associated with the second party, a propensity for the second party to prescribe, issue, or recommend a particular product associated with the second party, or a propensity for the second party to recommend against the particular product.

In some embodiments, the trained machine learning model may output multiple sentiment scores. For example, in the context of prescribing pharmaceutical compositions, HCPs tend to be conservative, so multiple meetings may be needed for the pharmaceutical maker or seller to provide sufficient information for the HCP to change prescription writing actions. For example, health care provider's may initially be conservative with new drugs because of the focus on health and safety of the patients. Accordingly, multiple meetings may be necessary to address concerns or questions with additional discussion of information such as scientific findings, field clinical data, and peer recommendations or finding. Multiple sentiment scores for multiple transcripts can show trends in propensity to write a desired prescription over time. In these embodiments, an input to the trained machine learning model at block 204 can include one or more sentiment values that had been output after evaluation of one or more other transcripts of one or more other meetings.

Further, in some embodiments, other data points from the CDP can be used as inputs to evaluation of the machine learning model. For example, predictive scoring values representing a propensity to purchase an item or service, which have been previously calculated in the CDP and are relevant to the same entity or pharmaceutical composition seller or maker, can be added as inputs in the evaluation stage. In some embodiments, "recency" values that represent a length of time since a meeting occurred, as represented in the transcript data, can be used as inputs. For example, transcript data that is more recent can be weighted higher in evaluation of the model.

At block 205, other digital engagement data representing engagement of the first party with digital assets of the second party is accessed. As referenced above, engagement data includes records, statistics, and/or metadata regarding interactions of the first party or agents thereof to interact with digital assets of the second party. Examples of the digital assets can include contact center transcripts, chat data or chat transcripts, websites, webinars, or other online tools in which conversations are captured. The engagement data can be obtained programmatically via calls to the CDP. The engagement data may be collected over time and stored in a database that associates the engagement data or records with the first party. The second computer may then select the digital engagement data by querying the database with an identification of the first party. In some embodiments, the engagement data may be filtered or selected based on more variables such as the particular domain of the transcript, a particular language of the transcript, or based on the particular action that is being predictively analyzed.

At block 206, a machine learning classifier is used to evaluate the first sentiment score and the engagement data to output a value indicative of a likelihood of the first party to take a particular action. A machine learning classifier is used, for example, by the second computer to analyze the engagement data and the first sentiment score and output the value. For example, the machine learning classifier may analyze each piece of data to determine the likelihood of the first party to take the action. In some embodiments, the machine learning classifier may output a binary YES or NO. In some embodiments, the machine learning classifier may classify the sentiment score along with classifying the engagement data to generate the value.

At decision block 207, the value is compared to a predetermined threshold. If the value is not greater than the predetermined threshold, then the value may be stored in a profile of the first party within a database at block 209. If the value is greater than the predetermined threshold, then a notification to a user computing device associated with the second party is transmitted at block 208. In some embodiments, the predetermined threshold may be manually set by an administrator or automatically updated based on rules associated with the second party. For example, the threshold may be adjusted based on a number of products associated with the particular action that the second party has in inventory, a price of the particular products, a number of available samples, and so on. The notification may be in the form of a push notification, an alarm, an email, text message, etc. The notification is configured to notify personnel that the particular action is likely to be taken. In some embodiments, the second computer may automatically submit an order to the second computer if the value is above the threshold, where the order specifying shipping a product associated with the event to the first party.

Propensity values, score values, or other output of the machine learning model that are generated in the foregoing manner can be used in and/or integrated with other systems of several kinds and for several purposes. Propensity values can be surfaced in graphical user interfaces or dashboards that are directed to users who are representatives of an entity interested in the outcome, such as pharmaceutical company representatives. Propensity values can be used to drive other actions. For example, if a propensity value is high, indicating a high likelihood of prescribing a pharmaceutical composition or taking other action, then the enterprise computing system 106 can be programmed to change the routing of a sample item or the scheduling of deliveries of sample items to be sooner. Conversely, if a propensity value is low, indicating a low likelihood of prescribing a pharmaceutical composition or taking other action, then the enterprise computing system 106 can be programmed to cancel the delivery of a sample item or the scheduling of deliveries of sample items to be later. Priority or ordering values could be changed.

Figure 3:
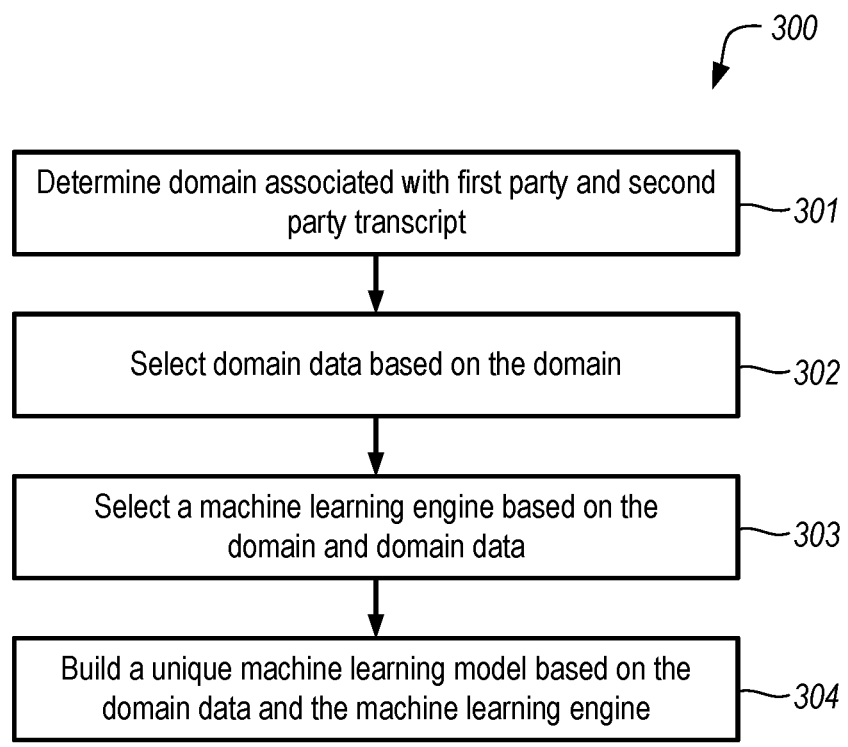
FIG. 3 illustrates an example computer-implemented process or algorithm for generating metadata for database tables useful in exploratory data analysis.

FIG. 3 illustrates an example computer-implemented process or algorithm for building or training a machine learning model using domain data. In the example of FIG. 3, a computer-implemented process 300 initiates execution at block 301 where a domain is determined. In some embodiments, the domain may be selected based on information associated with a natural language transcript that is to be analyzed. In some embodiments, the domain may be determined based on an identification of a first party, a second party, or particular person that appear in the transcript. In some embodiments, the domain may be determined based on a particular action that is to be analyzed. In some embodiments, the domain may be selected based on a geographic location of a party, language of the transcript, or based on an industry associated with the discussion of the transcript.

At block 302, domain data is selected based on the determined domain. For example, domain data may be selected by querying a database of domain data to select all data elements that are unique or associated with the determined domain. For instance, the domain data may be selected based on common terms in an industry, such as an industry associated with one of the parties or the transcript. In some embodiments, the domain data may be selected based on a language used by the first party or agent of the first party. In various embodiments, the domain data may be selected based on multiple variables such that the selected data is unique to the domain and/or the particular action that is being analyzed. The domain data may include information including words, phrases, or audio data including transform data and associated flags. For example, each object of the domain data may include flags that indicate an emotional category and/or score that is associated with the information.

At block 303, a machine learning model or type is selected based on the domain and domain data. The machine learning model or type may be selected from a list of available engines stored in a database or accessible over the network. In some embodiments, the second computer analyzes the domain and the domain data and references a lookup table of best machine learning model engines or types to select the machine learning model or type. In some embodiments, the machine learning model is selected based on an identification of the first party or the second party.

At block 304, a unique machine learning model is built using the domain data and the machine learning type. For example, the domain data may be used to train the selected machine learning model in order to output a unique, trained machine learning model that is able to accept transcript data, predict or classify emotional content of one or more portions of the transcript related to the first party, and output a sentiment score. For example, the flags of the domain data may train the machine learning model or type to identify emotional states or classification associated with particular audio data, words, or phrases and to aggregate and/or convolute the multiple data elements of the transcript data in order to output one or more sentiment scores within a range. In some embodiments, the sentiment score may be a "1" if the sentiment high, a "−1" if the sentiment is low, and a "0" if the sentiment is neutral.

2.3 Benefits and Improvements

The embodiments of this disclosure offer numerous benefits and improvements over prior approaches. The techniques of this disclosure are highly scalable as compared to custom scripting or other manual programming techniques. Embodiments of the computer systems allow for enterprises to create or build unique models to determine the likelihood of a second enterprise or person to take a particular action. That likelihood allows for the enterprise to better manage its resources and direct products with a more intelligent supply chain flow. Moreover, the embodiments described herein, improve the computing system and technological environment of the enterprise by allows the enterprise to create or build unique, trained models in order to transform a large amount of raw data into score data and further into data that is usable by the computing system and administrators to implement new processes or take actions.

Furthermore, in past practice, human intuition or heuristics based on memory or feelings have been used to determine the propensity of an HCP to prescribe a pharmaceutical composition and/or determine the next best actions to take after each digital meeting. Using embodiments of the disclosure, data-driven sentiment scores based on evidence represented in meeting transcription data, and digital engagement behavior of the HCP, can be evaluated using machine learning models to more objectively and accurately predict the propensity, whether the propensity is increasing or decreasing, and/or the next best actions to take in relation to a particular digital meeting.

3. Implementation Example—Hardware Overview

According to one embodiment, the techniques described herein are implemented by at least one computing device. The techniques may be implemented in whole or in part using a combination of at least one server computer and/or other computing devices that are coupled using a network, such as a packet data network. The computing devices may be hard-wired to perform the techniques, or may include digital electronic devices such as at least one application-specific integrated circuit (ASIC) or field programmable gate array (FPGA) that is persistently programmed to perform the techniques, or may include at least one general purpose hardware processor programmed to perform the techniques pursuant to program instructions in firmware, memory, other storage, or a combination. Such computing devices may also combine custom hard-wired logic, ASICs, or FPGAs with custom programming to accomplish the described techniques. The computing devices may be server computers, workstations, personal computers, portable computer systems, handheld devices, mobile computing devices, wearable devices, body mounted or implantable devices, smartphones, smart appliances, internetworking devices, autonomous or semi-autonomous devices such as robots or unmanned ground or aerial vehicles, any other electronic device that incorporates hard-wired and/or program logic to implement the described techniques, one or more virtual computing machines or instances in a data center, and/or a network of server computers and/or personal computers.

Figure 4:
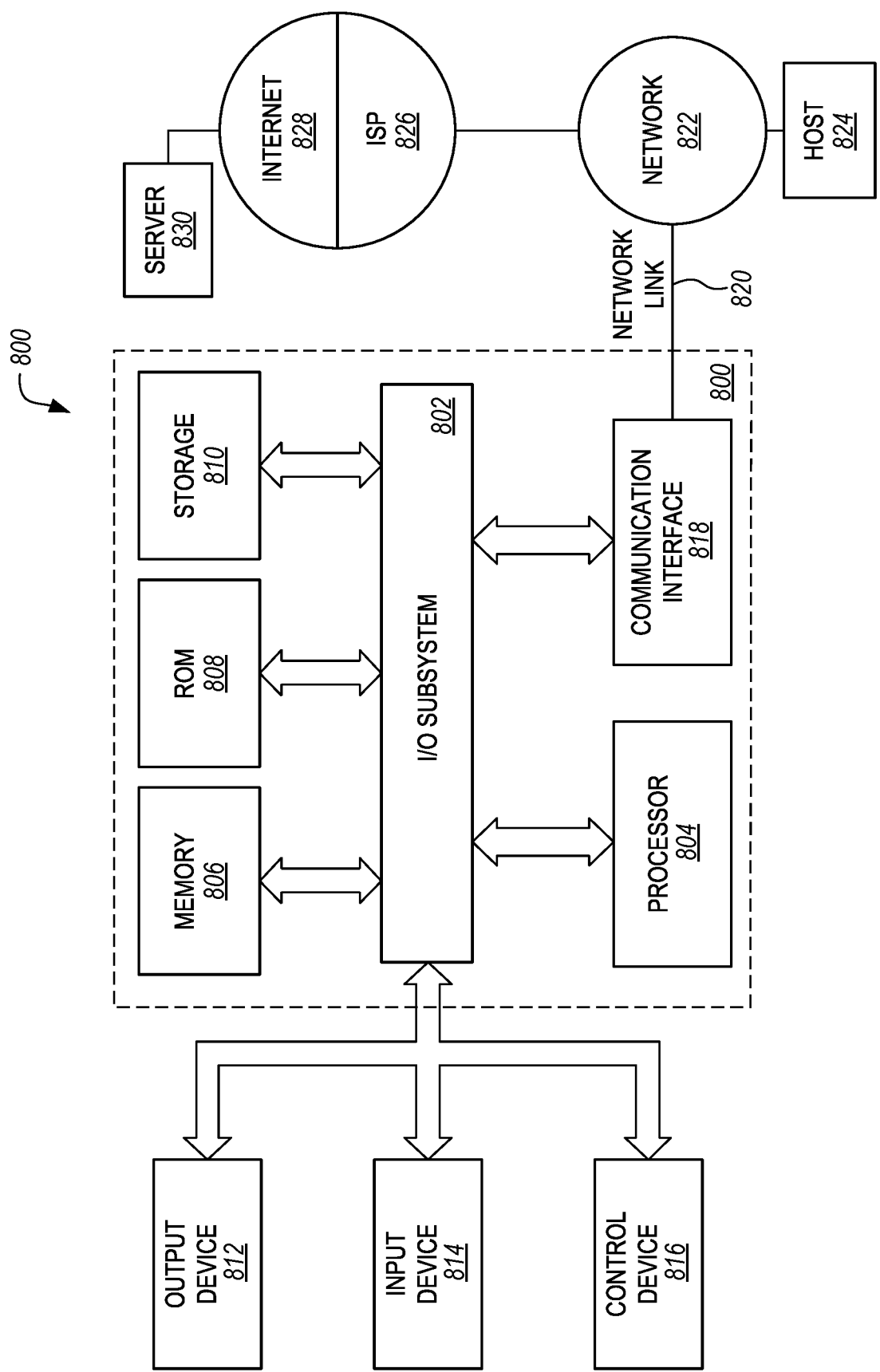
FIG. 4 illustrates a computer system with which one embodiment could be implemented.

FIG. 4 illustrates a computer system with which an embodiment may be implemented. In the example of FIG. 4, a computer system 800 and instructions for implementing the disclosed technologies in hardware, software, or a combination of hardware and software, are represented schematically, for example as boxes and circles, at the same level of detail that is commonly used by persons of ordinary skill in the art to which this disclosure pertains for communicating about computer architecture and computer systems implementations.

Computer system 800 includes an input/output (I/O) subsystem 802 which may include a bus and/or other communication mechanism(s) for communicating information and/or instructions between the components of the computer system 800 over electronic signal paths. The I/O subsystem 802 may include an I/O controller, a memory controller and at least one I/O port. The electronic signal paths are represented schematically in the drawings, for example as lines, unidirectional arrows, or bidirectional arrows.

At least one hardware processor 804 is coupled to I/O subsystem 802 for processing information and instructions. Hardware processor 804 may include, for example, a general-purpose microprocessor or microcontroller and/or a special-purpose microprocessor such as an embedded system or a graphics processing unit (GPU) or a digital signal processor or ARM processor. Processor 804 may comprise an integrated arithmetic logic unit (ALU) or may be coupled to a separate ALU.

Computer system 800 includes one or more units of memory 806, such as a main memory, which is coupled to I/O subsystem 802 for electronically digitally storing data and one or more sequences of instructions to be executed by processor 804. Memory 806 may include volatile memory such as various forms of random-access memory (RAM) or other dynamic storage device. Memory 806 also may be used for storing temporary variables or other intermediate information during execution of instructions to be executed by processor 804. Such instructions, when stored in non-transitory computer-readable storage media accessible to processor 804, can render computer system 800 into a special-purpose machine that is customized to perform the operations specified in the instructions.

Computer system 800 further includes non-volatile memory such as read only memory (ROM) 808 or other static storage device coupled to I/O subsystem 802 for storing information and instructions for processor 804. The ROM 808 may include various forms of programmable ROM (PROM) such as erasable PROM (EPROM) or electrically erasable PROM (EEPROM). A unit of persistent storage 810 may include various forms of non-volatile RAM (NVRAM), such as FLASH memory, or solid-state storage, magnetic disk or optical disk such as CD-ROM or DVD-ROM and may be coupled to I/O subsystem 802 for storing information and instructions. Storage 810 is an example of one or more non-transitory computer-readable storage media that may be used to store one or more sequences of instructions and data which when executed by the processor 804 cause performing computer-implemented methods to execute the techniques herein.

The instructions in memory 806, ROM 808 or storage 810 may comprise one or more sets of instructions that are organized as modules, methods, objects, functions, routines, or calls. The instructions may be organized as one or more computer programs, operating system services, or application programs including mobile apps. The instructions may comprise an operating system and/or system software; one or more libraries to support multimedia, programming or other functions; data protocol instructions or stacks to implement TCP/IP, HTTP or other communication protocols; file format processing instructions to parse or render files coded using HTML, XML, JPEG, MPEG or PNG; user interface instructions to render or interpret commands for a graphical user interface (GUI), command-line interface or text user interface; application software such as an office suite, internet access applications, design and manufacturing applications, graphics applications, audio applications, software engineering applications, educational applications, games or miscellaneous applications. The instructions may implement a web server, web application server or web client. The instructions may be organized as a presentation layer, application layer and data storage layer such as a relational database system using SQL or no SQL, an object store, a graph database, a flat file system or other data storage.

Computer system 800 may be coupled via I/O subsystem 802 to at least one output device 812. In one embodiment, output device 812 is a digital computer display. Examples of a display that may be used in various embodiments include a touch screen display or a light-emitting diode (LED) display or a liquid crystal display (LCD) or an e-paper display. Computer system 800 may include other type(s) of output devices 812, alternatively or in addition to a display device. Examples of other output devices 812 include printers, ticket printers, plotters, projectors, sound cards or video cards, speakers, buzzers or piezoelectric devices or other audible devices, lamps or LED or LCD indicators, haptic devices, actuators, or servos.

At least one input device 814 is coupled to I/O subsystem 802 for communicating signals, data, command selections or gestures to processor 804. Examples of input devices 814 include touch screens, microphones, still and video digital cameras, alphanumeric and other keys, keypads, keyboards, graphics tablets, image scanners, joysticks, clocks, switches, buttons, dials, slides, and/or various types of sensors such as force sensors, motion sensors, heat sensors, accelerometers, gyroscopes, and inertial measurement unit (IMU) sensors and/or various types of transceivers such as wireless, such as cellular or Wi-Fi, radio frequency (RF) or infrared (IR) transceivers and Global Positioning System (GPS) transceivers.

Another type of input device is a control device 816, which may perform cursor control or other automated control functions such as navigation in a graphical interface on a display screen, alternatively or in addition to input functions. Control device 816 may be a touchpad, a mouse, a trackball, or cursor direction keys for communicating direction information and command selections to processor 804 and for controlling cursor movement on an output device 812 such as a display. The input device may have at least two degrees of freedom in two axes, a first axis (e.g., x) and a second axis (e.g., y), that allows the device to specify positions in a plane. Another type of input device is a wired, wireless, or optical control device such as a joystick, wand, console, steering wheel, pedal, gearshift mechanism or other type of control device. An input device 814 may include a combination of multiple different input devices, such as a video camera and a depth sensor.

In another embodiment, computer system 800 may comprise an internet of things (IoT) device in which one or more of the output devices 812, input device 814, and control device 816 are omitted. Or, in such an embodiment, the input device 814 may comprise one or more cameras, motion detectors, thermometers, microphones, seismic detectors, other sensors or detectors, measurement devices or encoders and the output device 812 may comprise a special-purpose display such as a single-line LED or LCD display, one or more indicators, a display panel, a meter, a valve, a solenoid, an actuator or a servo.

When computer system 800 is a mobile computing device, input device 814 may comprise a global positioning system (GPS) receiver coupled to a GPS module that is capable of triangulating to a plurality of GPS satellites, determining and generating geo-location or position data such as latitude-longitude values for a geophysical location of the computer system 800. Output device 812 may include hardware, software, firmware and interfaces for generating position reporting packets, notifications, pulse or heartbeat signals, or other recurring data transmissions that specify a position of the computer system 800, alone or in combination with other application-specific data, directed toward host computer 824 or server computer 830.

Computer system 800 may implement the techniques described herein using customized hard-wired logic, at least one ASIC or FPGA, firmware and/or program instructions or logic which when loaded and used or executed in combination with the computer system causes or programs the computer system to operate as a special-purpose machine. According to one embodiment, the techniques herein are performed by computer system 800 in response to processor 804 executing at least one sequence of at least one instruction contained in main memory 806. Such instructions may be read into main memory 806 from another storage medium, such as storage 810. Execution of the sequences of instructions contained in main memory 806 causes processor 804 to perform the process steps described herein. In alternative embodiments, hard-wired circuitry may be used in place of or in combination with software instructions.

The term "storage media" as used herein refers to any non-transitory media that store data and/or instructions that cause a machine to operation in a specific fashion. Such storage media may comprise non-volatile media and/or volatile media. Non-volatile media includes, for example, optical or magnetic disks, such as storage 810. Volatile media includes dynamic memory, such as memory 806. Example forms of storage media include, for example, a hard disk, solid state drive, flash drive, magnetic data storage medium, any optical or physical data storage medium, memory chip, or the like.

Storage media is distinct from but may be used in conjunction with transmission media. Transmission media participates in transferring information between storage media. For example, transmission media includes coaxial cables, copper wire and fiber optics, including the wires that comprise a bus of I/O subsystem 802. Transmission media can also take the form of acoustic or light waves, such as those generated during radio-wave and infra-red data communications.

Various forms of media may be involved in carrying at least one sequence of at least one instruction to processor 804 for execution. For example, the instructions may initially be carried on a magnetic disk or solid-state drive of a remote computer. The remote computer can load the instructions into its dynamic memory and send the instructions over a communication link such as a fiber optic or coaxial cable or telephone line using a modem. A modem or router local to computer system 800 can receive the data on the communication link and convert the data to a format that can be read by computer system 800. For instance, a receiver such as a radio frequency antenna or an infrared detector can receive the data carried in a wireless or optical signal and appropriate circuitry can provide the data to I/O subsystem 802 such as place the data on a bus. I/O subsystem 802 carries the data to memory 806, from which processor 804 retrieves and executes the instructions. The instructions received by memory 806 may optionally be stored on storage 810 either before or after execution by processor 804.

Computer system 800 also includes a communication interface 818 coupled to I/O subsystem 802. Communication interface 818 provides a two-way data communication coupling to network link(s) 820 that are directly or indirectly connected to at least one communication networks, such as a network 822 or a public or private cloud on the Internet. For example, communication interface 818 may be an Ethernet networking interface, integrated-services digital network (ISDN) card, cable modem, satellite modem, or a modem to provide a data communication connection to a corresponding type of communications line, for example an Ethernet cable or a metal cable of any kind or a fiber-optic line or a telephone line. Network 822 broadly represents a local area network (LAN), wide-area network (WAN), campus network, internetwork or any combination thereof. Communication interface 818 may comprise a LAN card to provide a data communication connection to a compatible LAN, or a cellular radiotelephone interface that is wired to send or receive cellular data according to cellular radiotelephone wireless networking standards, or a satellite radio interface that is wired to send or receive digital data according to satellite wireless networking standards. In any such implementation, communication interface 818 sends and receives electrical, electromagnetic or optical signals over signal paths that carry digital data streams representing various types of information.

Network link 820 typically provides electrical, electromagnetic, or optical data communication directly or through at least one network to other data devices, using, for example, satellite, cellular, Wi-Fi, or BLUETOOTH technology. For example, network link 820 may provide a connection through a network 822 to a host computer 824.

Furthermore, network link 820 may provide a connection through network 822 or to other computing devices via internetworking devices and/or computers that are operated by an Internet Service Provider (ISP) 826. ISP 826 provides data communication services through a world-wide packet data communication network represented as internet 828. A server computer 830 may be coupled to internet 828. Server computer 830 broadly represents any computer, data center, virtual machine or virtual computing instance with or without a hypervisor, or computer executing a containerized program system such as DOCKER or KUBERNETES. Server computer 830 may represent an electronic digital service that is implemented using more than one computer or instance and that is accessed and used by transmitting web services requests, uniform resource locator (URL) strings with parameters in HTTP payloads, API calls, app services calls, or other service calls. Computer system 800 and server computer 830 may form elements of a distributed computing system that includes other computers, a processing cluster, server farm or other organization of computers that cooperate to perform tasks or execute applications or services. Server computer 830 may comprise one or more sets of instructions that are organized as modules, methods, objects, functions, routines, or calls. The instructions may be organized as one or more computer programs, operating system services, or application programs including mobile apps. The instructions may comprise an operating system and/or system software; one or more libraries to support multimedia, programming or other functions; data protocol instructions or stacks to implement TCP/IP, HTTP or other communication protocols; file format processing instructions to parse or render files coded using HTML, XML, JPEG, MPEG or PNG; user interface instructions to render or interpret commands for a graphical user interface (GUI), command-line interface or text user interface; application software such as an office suite, internet access applications, design and manufacturing applications, graphics applications, audio applications, software engineering applications, educational applications, games or miscellaneous applications. Server computer 830 may comprise a web application server that hosts a presentation layer, application layer and data storage layer such as a relational database system using structured query language (SQL) or no SQL, an object store, a graph database, a flat file system or other data storage.

Computer system 800 can send messages and receive data and instructions, including program code, through the network(s), network link 820 and communication interface 818. In the Internet example, a server computer 830 might transmit a requested code for an application program through Internet 828, ISP 826, local network 822 and communication interface 818. The received code may be executed by processor 804 as it is received, and/or stored in storage 810, or other non-volatile storage for later execution.

The execution of instructions as described in this section may implement a process in the form of an instance of a computer program that is being executed, and consisting of program code and its current activity. Depending on the operating system (OS), a process may be made up of multiple threads of execution that execute instructions concurrently. In this context, a computer program is a passive collection of instructions, while a process may be the actual execution of those instructions. Several processes may be associated with the same program; for example, opening up several instances of the same program often means more than one process is being executed. Multitasking may be implemented to allow multiple processes to share processor 804. While each processor 804 or core of the processor executes a single task at a time, computer system 800 may be programmed to implement multitasking to allow each processor to switch between tasks that are being executed without having to wait for each task to finish. In an embodiment, switches may be performed when tasks perform input/output operations, when a task indicates that it can be switched, or on hardware interrupts. Time-sharing may be implemented to allow fast response for interactive user applications by rapidly performing context switches to provide the appearance of concurrent execution of multiple processes simultaneously. In an embodiment, for security and reliability, an operating system may prevent direct communication between independent processes, providing strictly mediated and controlled inter-process communication functionality.

In the foregoing specification, embodiments of the invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction.

What is claimed is:

1. A computer-implemented method, comprising:
    establishing a programmatic connection comprising an application protocol interface (API), an app-specific protocol, or a parametrized HTTP call between a first computer and a second computer;
    receiving, at the second computer from the first computer using the programmatic connection, a natural language transcript in electronic digital format of a conversation between a first party and a second party;
    building a trained machine learning model by:
        based on metadata stored with the transcript and specifying a language of the transcript, one or more identifications of the first party and/or the second party, one or more geographic locations of the first party and/or the second party, selecting a machine learning model having a particular machine learning type from among a FLARE model, a spaCY model, a BERT model, a RoBERTa model, or a Clinical-BERT model;
        querying a database of domain data to select domain data comprising data elements are associated with healthcare or pharmaceuticals, based on the transcript and/or the parties or organizations within the transcript, the domain data comprising labeled conversation data of conversations using scientific, medical, and technical terminology in healthcare or pharmaceuticals and a taxonomy of sentiments, the domain data comprising a digitally stored data table storing a plurality of words or phrases and one or more associated scores that are unique to a category of emotional data; and
        fine-tune training the machine learning model using the domain data to form the trained machine learning model to accept the natural language transcript as an input, predict or classify emotional content of one or more portions of the transcript related to the first party, and output a sentiment score, the sentiment score representing a likelihood of the first party to take an action;
    accessing the trained machine learning model;
    determining a first sentiment score related to the first party via inputting the natural language transcript into the trained machine learning model and evaluating the natural language transcript using single shot detection;
    programmatically querying a digital engagement data database with an identification of the first party and receiving, in response, digital engagement data representing engagement of the first party with digital assets associated with the second party by the second computer programmatically via calls to a customer data platform querying a database of the customer data platform storing one or more of records, statistics, and metadata of conversations from contact center transcripts, chat data or chat transcripts, websites, or webinars collected over time;
    evaluating, using a machine learning classifier, the first sentiment score and the digital engagement data to output a value indicative of the likelihood of the first party to take a particular action; and
    determining whether the value is above a threshold, and if so, automatically sending to a computer device associated with the second party an order specifying shipping a product associated with the particular action to the first party.

2. The computer-implemented method of claim 1, further comprising accessing the trained machine learning model and determining multiple sentiment scores related to the first party via inputting multiple natural language transcripts corresponding to multiple meetings into the trained machine learning model and evaluating the multiple natural language transcripts using single shot detection.

3. The computer-implemented method of claim 1, the first computer comprising a teleconferencing computing system having a transcription engine.

4. The computer-implemented method of claim 1, further comprising:
    receiving, at the second computer from the first computer, a second natural language transcript of a second conversation between the first party and the second party;
    evaluating, using the machine learning model, the second natural language transcript to output a second sentiment score related to the first party in a domain associated with the second party;
    automatically updating the value with the second sentiment score;
    determining whether the value is above the threshold, and if so, automatically sending a notification to a computer device associated with the second party.

5. The computer-implemented method of claim 1, further comprising filtering the natural language transcript to exclude data related to portions of the natural language transcript that are indicative of talking by the second party.

6. The computer-implemented method of claim 1, further comprising surfacing, in a graphical user interface or dashboard, a propensity value comprising the value indicative of the likelihood of the first party to take the particular action.

7. The computer-implemented method of claim 1, further comprising, in response to the value indicative of the likelihood of the first party to take the particular action, changing a routing of a sample item or canceling a delivery of the sample item.

8. The computer-implemented method of claim 1, the emotional data or classifications including information related to categories that include sadness, anger, contempt, disgust, surprise, fear, and agreeableness.

9. The computer-implemented method of claim 1, wherein the likelihood of the first party to take the action corresponds to a purchase of a particular product associated with the second party, a propensity for the second party to prescribe, issue, or recommend a particular product associated with the second party, or a propensity for the second party to recommend against the particular product.

10. The computer-implemented method of claim 1, the first party being a healthcare provider, the particular action comprising the first party writing a prescription for a particular pharmaceutical composition.

11. One or more non-transitory computer-readable storage media storing one or more sequences of program instructions which, when executed using one or more processors, cause the one or more processors to execute:
    establishing a programmatic connection comprising an application protocol interface (API), an app-specific protocol, or a parametrized HTTP call between a first computer and a second computer;
    receiving, at the second computer from the first computer using the programmatic connection, a natural language transcript in electronic digital format of a conversation between a first party and a second party;

building a trained machine learning model by:
based on metadata stored with the transcript and specifying a language of the transcript, one or more identifications of the first party and/or the second party, one or more geographic locations of the first party and/or the second party, selecting a machine learning model having a particular machine learning type from among a FLARE model, a spaCY model, a BERT model, a RoBERTa model, or a Clinical-BERT model;

querying a database of domain data to select domain data comprising data elements are associated with healthcare or pharmaceuticals, based on the transcript and/or the parties or organizations within the transcript, the domain data comprising labeled conversation data of conversations using scientific, medical, and technical terminology in healthcare or pharmaceuticals and a taxonomy of sentiments, the domain data comprising a digitally stored data table storing a plurality of words or phrases and one or more associated scores that are unique to a category of emotional data; and fine-tune training the machine learning model using the domain data to form the trained machine learning model to accept the natural language transcript as an input, predict or classify emotional content of one or more portions of the transcript related to the first party, and output a sentiment score, the sentiment score representing a likelihood of the first party to take an action;

accessing the trained machine learning model;

determining a first sentiment score related to the first party via inputting the natural language transcript into the trained machine learning model and evaluating the natural language transcript using single shot detection;

programmatically querying a digital engagement data database with an identification of the first party and receiving, in response, digital engagement data representing engagement of the first party with digital assets associated with the second party by the second computer programmatically via calls to a customer data platform querying a database of the customer data platform storing one or more of records, statistics, and metadata of conversations from contact center transcripts, chat data or chat transcripts, websites, or webinars collected over time;

evaluating, using a machine learning classifier, the first sentiment score and the digital engagement data to output a value indicative of the likelihood of the first party to take a particular action; and determining whether the value is above a threshold, and if so, automatically sending to a computer device associated with the second party an order specifying shipping a product associated with the particular action to the first party.

12. The one or more non-transitory computer-readable storage media of claim 11, further comprising sequences of program instructions which, when executed using the one or more processors, cause the one or more processors to execute accessing the trained machine learning model and determining multiple sentiment scores related to the first party via inputting multiple natural language transcripts corresponding to multiple meetings into the trained machine learning model and evaluating the multiple natural language transcripts using single shot detection.

13. The one or more non-transitory computer-readable storage media of claim 11, the first computer comprising a teleconferencing computing system having a transcription engine.

14. The one or more non-transitory computer-readable storage media of claim 11, further comprising sequences of program instructions which, when executed using the one or more processors, cause the one or more processors to execute:
receiving, at the second computer from the first computer, a second natural language transcript of a second conversation between the first party and the second party;
evaluating, using the machine learning model, the second natural language transcript to output a second sentiment score related to the first party in a domain associated with the second party;
automatically updating the value with the second sentiment score;
determining whether the value is above the threshold, and if so, automatically sending a notification to a computer device associated with the second party.

15. The one or more non-transitory computer-readable storage media of claim 11, further comprising sequences of program instructions which, when executed using the one or more processors, cause the one or more processors to execute filtering the natural language transcript to exclude data related to portions of the natural language transcript that are indicative of talking by the second party.

16. The one or more non-transitory computer-readable storage media of claim 11, further comprising sequences of program instructions which, when executed using the one or more processors, cause the one or more processors to execute surfacing, in a graphical user interface or dashboard, a propensity value comprising the value indicative of the likelihood of the first party to take the particular action.

17. The one or more non-transitory computer-readable storage media of claim 11, further comprising sequences of program instructions which, when executed using the one or more processors, cause the one or more processors to execute, in response to the value indicative of the likelihood of the first party to take the particular action, changing a routing of a sample item or canceling a delivery of the sample item.

18. The one or more non-transitory computer-readable storage media of claim 11, the emotional data or classifications including information related to categories that include sadness, anger, contempt, disgust, surprise, fear, and agreeableness.

19. The one or more non-transitory computer-readable storage media of claim 11, wherein the likelihood of the first party to take the action corresponds to a purchase of a particular product associated with the second party, a propensity for the second party to prescribe, issue, or recommend a particular product associated with the second party, or a propensity for the second party to recommend against the particular product.

20. The one or more non-transitory computer-readable storage media of claim 11, the first party being a healthcare provider, the particular action comprising the first party writing a prescription for a particular pharmaceutical composition.

* * * * *